(12) United States Patent
Jensen (10) Patent No.: US 10,845,265 B2
(45) Date of Patent: Nov. 24, 2020

(54) GAS INDICATOR

(71) Applicant: Thanner A/S, Esbjerg (DK)

(72) Inventor: Peter Jensen, Esbjerg (DK)

(73) Assignee: Thanner A/S, Esbjerg (DK)

( * ) Notice: Subject to any disclaimer, the term of this patent is extended or adjusted under 35 U.S.C. 154(b) by 0 days.

(21) Appl. No.: 16/188,628

(22) Filed: Nov. 13, 2018

(65) Prior Publication Data

US 2019/0145849 A1 May 16, 2019

(30) Foreign Application Priority Data

Nov. 13, 2017 (DK) .................................. 2017 70857
Nov. 30, 2017 (DK) .................................. 2017 70897

(51) Int. Cl.
| | | |
|---|---|---|
| *G08B 23/00* | (2006.01) | |
| *G01M 3/22* | (2006.01) | |
| *G01N 33/00* | (2006.01) | |
| *B63C 9/04* | (2006.01) | |
| *G01N 31/22* | (2006.01) | |
| *G01N 21/78* | (2006.01) | |

(52) U.S. Cl.
CPC ............... *G01M 3/227* (2013.01); *B63C 9/04* (2013.01); *G01N 31/223* (2013.01); *G01N 33/004* (2013.01); *B63C 2009/042* (2013.01); *G01N 21/783* (2013.01)

(58) Field of Classification Search
CPC .... B63C 2009/042; B63C 9/04; G01M 3/227; G01N 21/783; G01N 31/223; G01N 33/004

USPC ......................................................... 340/984
See application file for complete search history.

(56) References Cited

U.S. PATENT DOCUMENTS

| | | | | |
|---|---|---|---|---|
| 4,003,709 A | * | 1/1977 | Eaton ...................... | G01N 31/22 422/86 |
| 4,728,499 A | * | 3/1988 | Fehder .................. | G01N 31/223 422/401 |
| 4,994,117 A | * | 2/1991 | Fehder .................. | G01N 31/223 128/207.14 |
| 5,407,829 A | * | 4/1995 | Wolfbeis ................. | G01N 31/22 422/400 |
| 5,439,648 A | * | 8/1995 | Balderson ............. | A23L 3/3418 422/421 |
| 5,653,941 A | * | 8/1997 | Veretto ................ | G01N 21/783 422/410 |

(Continued)

FOREIGN PATENT DOCUMENTS

| | | |
|---|---|---|
| DE | 2854628 A1 | 6/1980 |
| EP | 0627363 A1 | 12/1994 |

(Continued)

*Primary Examiner* — Naomi J Small
(74) *Attorney, Agent, or Firm* — James Creighton Wray (57) ABSTRACT

The object of the invention is to provide means and method of monitoring target gas content in gas tight membrane enclosing a volume containing an object. The visible gas indicator comprises means for being fastened to a gas tight membrane enclosing a volume containing an object, where the gas indicator comprises a chamber having a transparent window. The chamber is in gas communication with the interior of the volume. The window is arranged outside said volume, and a substrate is arranged inside said chamber and visible from outside said volume, where said substrate changes colours when exposed to a target gas.

12 Claims, 4 Drawing Sheets

(56) References Cited

U.S. PATENT DOCUMENTS

| | | | |
|---|---|---|---|
| 5,783,110 A | 7/1998 | Verdicchio | |
| 5,951,909 A | 9/1999 | Verdicchio | |
| 6,306,620 B1 | 10/2001 | Templeton | |
| 7,854,347 B2 * | 12/2010 | Wang | B63C 9/24 222/5 |
| 8,192,243 B2 * | 6/2012 | Jorgensen | B63C 9/22 441/35 |
| 8,292,680 B1 * | 10/2012 | Herr | F16L 15/006 441/41 |
| 2004/0241635 A1 | 12/2004 | Buckley | |
| 2005/0066707 A1 * | 3/2005 | Katsuki | G01N 33/005 73/23.21 |
| 2005/0130516 A1 * | 6/2005 | Courtney | B63C 9/24 441/92 |
| 2009/0232861 A1 * | 9/2009 | Wright | G06Q 30/018 424/405 |
| 2012/0264219 A1 * | 10/2012 | Sinclair | G01M 3/042 436/3 |

FOREIGN PATENT DOCUMENTS

| | | |
|---|---|---|
| EP | 1266944 A1 | 12/2002 |
| EP | 2977755 A1 | 1/2016 |
| WO | 9612659 A1 | 5/1996 |
| WO | 02094672 A1 | 11/2002 |

* cited by examiner

GAS INDICATOR

This application claims the benefit of Danish Application No. PA 2017 70857 filed Nov. 13, 2017 and Danish Application No. PA 2017 70897 filed Nov. 30, 2017, which are hereby incorporated by reference in their entirety as if fully set forth herein.

FIELD OF THE INVENTION

The present invention relates to means for monitoring a target gas inside a container storing an object. One particular use of the invention is to monitor carbon dioxide inside a container storing an inflatable life raft.

BACKGROUND OF THE INVENTION

A number of various objects are typically stored in containers in order to protect the objects from the ambient environment, in order to provide extended life expectancy for the objects. Some of these objects are provided with gas canisters, such that the object may be inflated—an example of such an object is an inflatable life raft. Other examples of objects may be inflatable structures such as tents, boats, surfboards, slides, bouncing castles, life preservers etc. As an example of an object, an inflatable life raft will be used in the following explanation of the invention, but it is contemplated that the invention is usable with any type of inflatable object.

Inflatable life rafts are well-known lifesaving equipment. For protecting the inflatable life raft it is known to place the inflatable life raft in a vacuum bag and the vacuum bag is often stored in a container or another bag. The container or bag is normally secured on a ship or vessel and is normally only dismounted when an accident occurs or when the inflatable life raft is to be serviced.

The maintenance of the inflatable life raft may take place on the ship or the inflatable life raft must be sent to a service station on land. The maintenance must take place at regular intervals for safety reasons, to ensure the functionality of the inflatable life raft.

Depending on jurisdiction, life rafts are required to have service at regular intervals, for example every 2½ or 4-5 years depending on make and legislation. During service the life raft is inflated and visually inspected. In this process the $CO_2$ canister (used for inflating the raft) is replaced.

It is desirable to be able to evaluate the life raft without unpacking and inflating the life raft, or without damaging the vacuum bag. Especially the carbon dioxide content of the gas inside the bag must be monitored, to determine whether the carbon dioxide canister is leaking carbon dioxide and thereby losing its inflating capacity.

It is well-known that the maintenance and monitoring of the condition of the vacuum-packed inflatable life raft can be performed by using e.g. sensors connected to a monitoring display for example by wireless communication. A measuring device is located inside the container of the vacuum-packed inflatable life-raft, measuring the status of different parameters, such as humidity and carbon dioxide level etc. A measuring device inside the container of the vacuum-packed inflatable life raft is able to transfer the parameters to a portable monitoring device placed outside the container by using wireless communication or alternatively a plug placed outside the vacuum-packed inflatable life raft. The solution is expensive, because there must be a measuring device inside the container, and a portable monitoring device is also required as well.

Due to safety regulations, the periodic inspections are time-consuming, expensive, and restricting. The solution provided, as mentioned above, is complicated and expensive, both in the production process and in the maintenance process of the vacuum-packed inflatable life raft.

It is well known to use compounds which will change appearance/colour when exposed to certain liquids or gasses.

In some examples, as for example suggested in EP 2977755 a pH indicator is mounted in a wall, such that the pH indicator is in communication with the interior of a refrigerator. As some (organic) product goes bad inside the refrigerator the ripening or rotting will generate various gasses. By providing a pH sensor the generation of gasses is detected and signaled to the outside of the refrigerator by means of a colour change in the pH sensor.

A similar problem is addressed in U.S. Pat. No. 4,003,709. Here the decay of foodstuff and the thereby generated gasses are detected by a CO2 detector, designed to register elevated levels of CO2 in the measurement environment. The device consists of a liquid solution of calcium hydroxide encapsulated in a microporous membrane, allowing gasses from the food stuff to permeate into the liquid solution.

Both these devices are very specific for detecting ripening or decay in organic produce. For applications in encapsulated objects having an embedded CO2 canister, these types of indications are not sufficient or applicable. Due to the very high security requirements for example for life rafts, very clear indications are necessary. It is not a question of the degree of gas present, but whether or not the target gas is present. With pH a number of other factors may influence the value, and not only/specifically the presence of a target gas.

OBJECT OF THE INVENTION

The object of the invention is to provide means and method to monitoring a target gas content in a gas tight membrane enclosing a volume containing an object, which addresses the problem regarding the complicated and expensive maintenance and monitoring of gas leak inside a gas tight membrane and additionally provides a number of further advantages.

DESCRIPTION OF THE INVENTION

The present invention addresses this by providing a visible gas indicator, where said indicator comprises fastening means for a gas tight membrane enclosing a gas evacuated volume containing an object, where said gas indicator comprises a chamber having a transparent window, wherein the gas indicator has a main tube, where the window is arranged in a first end of the main tube, where said chamber is in gas communication through said main tube with the interior of the volume, and said window is arranged outside said volume, and where a substrate is arranged inside said chamber and visible from outside said volume, where said substrate changes colours when exposed to a target gas. The visible gas indicator contains a substrate that changes colours, e g amine beads. The colour changing amine beads are known from other processes for removing carbon dioxide from gasses.

The feature that the membrane encloses a gas evacuated volume shall be understood as any gas, typically air, has been (substantially) evacuated from the volume enclosed by the membrane, to such an extent that a substantial underpressure will be present inside the enclosed volume in comparison to the ambient environment. Consequently if a target gas suddenly is present in the enclosed volume there may generally speaking be two sources: either a leak in the membrane or the CO2 canister may leak and be faulty. Typically a leak letting ambient air in will have a very low CO2 content (<0.5%) whereas a faulty canister leaking CO2 into an otherwise empty enclosure immediately will activate substrate and change colour.

Although the invention will be explained in many instances below with reference to a life raft, where the raft itself is packed inside a gas tight membrane (often evacuated from air—vacuum packed), the invention is, as will be recognized by a skilled person useful in any instance where it is desirable to register if a target gas is present/has leaked inside an otherwise gas tight closed volume, regardless of whether or not said volume has been evacuated from air.

A visible gas indicator is provided by the invention, where said gas indicator comprises fastening means to a gas tight membrane enclosing a volume containing an object, where the gas indicator comprises a chamber having a transparent window. The chamber is in gas communication with the interior of the volume. The window is arranged outside said volume, and the substrate is arranged inside the chamber and visible from outside said volume. The substrate changes colours when exposed to a target gas.

A visual gas indicator reveals a target gas inside a gas tight membrane enclosing an object and a volume of gas or a gas evacuated bag when a target gas is released inside the volume. The indication of presence of the target gas is quickly revealed by visually monitoring the gas indicator. When a target gas is present, the colour of the substrate contained in the gas indicator changes.

The $CO_2$ gas canister provided with the (vacuum-)packed inflatable life raft may be evaluated without unpacking and inflating the life raft, or without damaging the vacuum packed gas tight membrane. Thereby is it possible to prolong the intervals between inspections, without lowering the degree of operating safety. This will save time and costs for the user, especially if the inflatable life rafts need to be evaluated by opening the gas tight membrane. The gas tight membrane may, after inspection, be sealed again. At this point the opening in the membrane in which the gas indicator is arranged, may be used for installing a new gas indicator. Maintenance will therefore be fast and cost less.

In an advantageous embodiment of the invention, the target gas is carbon dioxide and the substrate contains amines.

Carbon dioxide gas is often being used when a life raft is inflated. Especially the carbon dioxide content of the gas inside the bag must therefore be monitored, to determine whether the carbon dioxide canister is leaking carbon dioxide into the bag and thereby losing the inflating capacity compromising the safety. Therefore one of the examples of target gasses may be carbon dioxide.

CCS or carbon capture and storage is normally used as a climate change solution that works to safely remove carbon dioxide from exhaust gasses of e.g. power plants and industrial processes before the carbon dioxide reaches the atmosphere. One of the methods uses a chemical process involving amines in the shape of beads, which removes the carbon dioxide from e.g. exhaust, by absorbing/storing the carbon dioxide inside the beads. The amine beads will easily change colours, e.g. from white to purple, when exposed to carbon dioxide. Once the amine cannot absorb more carbon dioxide, the beads will be able to discharge the captured carbon dioxide, when heat is applied. The beads can then be reused again and again.

When using the amine beads as a substrate arranged inside the chamber of the indicator, the amine beads will change from one colour when carbon dioxide is not present in the chamber (and thereby inside the gastight membrane), to another colour when detecting carbon dioxide in the chamber. Another target gas may be detected instead of carbon dioxide, when choosing another substrate arranged inside the chamber.

In a further advantageous embodiment of the invention the gas indicator has a main tube, where the window is arranged in a first end of the main tube. The tube is provided with a thread on the outside, such that two nuts can be screwed onto the thread. The nuts comprise opposing flanges, such that when the nuts are screwed onto the thread on the main tube and towards each other, the flanges will be on opposing sides of the gas tight membrane such that the nuts create a gas tight connection by squeezing against the membrane.

When integrating the gas indicator into the gas tight membrane, the gas indicator comprises a chamber having a transparent window, which may be arranged outside the volume. The gas indicator comprises a main tube providing the gas communication between the volume inside the gas tight membrane and the chamber. In order to preserve the gas tight membrane, the gas indicator must be attached to the gas tight membrane with a gas tight connection. The gas tight connection may be provided by using flanges on opposite sides of the gas tight membrane as described above with reference to the nuts. When the membrane is arranged between the flanges, the flanges are pressed together, by using e.g. nuts, rivets or clamps. To ensure the gas tight connection between the flanges and the membrane, a sealing compound may be provided between the flanges and the membrane before the flanges are pressed or screwed together.

The window is arranged in the first end of the main tube, and the chamber containing the substrate will then be visible from outside the gas tight membrane. The second end of the main tube is then located inside the gas tight membrane. If the target gas occurs inside the volume of the gas tight membrane, the main tube may lead the gas through to the chamber, and the target gas may be detected by causing the substrate to change colours.

In a still further advantageous embodiment of the invention, the gas indicator has a main tube. The window is arranged in a first end of the main tube where adjacent a second opposite end a flange is arranged extending radially away from said main tube.

The gas indicator may be attached to the gas tight membrane with a gas tight connection by sealing the flange provided on the main tube to the membrane. The chamber of the gas indicator may be sealed directly to the membrane. The sealing may be provided by glue/adhesive or by ultrasonic welding, or similar method, insuring a gas tight connection. The gas indicator may be provided before or after sealing the membrane that encloses a volume which contains an object.

In a further advantageous embodiment of the invention the main tube between the flange and a distance towards the window is provided with a thread, and a nut having a flange extending radially from said nut, is screwed onto the thread on the main tube, such that the gas tight membrane material may be arranged between the flange on the main tube and the flange on the nut.

The gas indicator may be assembled from the inside of the membrane, passing the window end of the main tube through an aperture provided in the membrane, leaving the flange of the main tube inside the membrane. The gas tight connection may be provided by using flanges on opposite sides of the gas tight membrane. The nuts, rivets or clamps may therefore be provided from the outside of the membrane, pressing the flange provided on the nut against the flange on the main tube, by screwing the nut onto the thread on the main tube. The membrane is arranged between the flanges providing a gas tight connection when the flanges are pressed together. To ensure the gas tight connection between the flanges and the membrane, a sealing compound may be provided between and/or around the flanges and the membranes.

In a still further advantageous embodiment of the invention, in addition to the fastening means to a gas tight membrane enclosing a volume containing an object, a further second means are provided for fastening the gas indicator to a container inside which the gas tight membrane enclosing the volume with the object is arranged, said window being visible on the outside of the container.

When the gas indicator is fastened to the gas tight membrane, the gas tight membrane enclosing a volume containing an object, e.g. an inflatable life raft, is placed inside a container or a bag. To monitor the gas indicator from the outside of the container, the window of the gas indicator must be visible from the outside, either by arranging a part of the gas indicator through an aperture in the container surface or by adding a window or transparent plate in the container, such that the gas indicator may be observed though the container.

In a further advantageous embodiment of the invention the second means comprises one or more second set of nuts which may be screwed onto the thread on the main tube.

The window of the gas indicator must be visible from the outside, and the window or a part of the window of the gas indicator may be lead through an aperture in the container and fastened to the surface of the container by means of e.g. nuts, screws or clamps. The gas indicator will then be visible from the outside of the container.

In a still further advantageous embodiment of the invention, the material of said gas indicator is manufactured from the following materials or combination of materials: stainless steel, aluminum, plastic, modified polymers.

The gas indicator may be used in a gas tight membrane containing an inflatable life raft. A container or bag containing the gas tight membrane is normally secured on a ship or vessel. Due to the harsh environment caused by the sea water, the gas indicator must have a high resistance to corrosion and staining. By choosing a material with a high resistance, especially the outer parts of the gas indicator which may be in contact with e.g. moisture and water, the life span of the gas indicator may be considerably prolonged. This may result in a low maintenance rate, and thereby prolong the interval between inspections, without lowering the degree of operating safety.

The invention also provides further advantageous embodiment of a visible gas indicator on the outside of an enclosed volume, where the target gas is carbon dioxide and the substrate contains amines and where said visible gas indicator comprises a chamber having a transparent window, where said chamber is in gas communication with the interior of the volume, and said window is arranged outside said volume, and the substrate is arranged inside said chamber and visible from outside said volume, where said substrate changes colours when exposed to carbon dioxide, where said gas indicator has a main tube, where the window is arranged in a first end of the main tube, and where a flange is provided extending radially from the main tube such that a gas tight connection is established between the flange and the membrane.

The invention provides a simple and efficient solution to visual monitoring of the carbon dioxide presence inside a packed inflatable life raft, by using a visible gas indicator. By using a visible gas indicator attached to the packed inflatable life raft the monitoring is easily accessed at all time. Also the production process will be optimized as regards time and costs, because the visible gas indicator is easily produced and attached to the packed inflatable life raft.

The invention also provides a further advantageous embodiment where the main tube is provided with a thread on the outside, and where two nuts can be screwed onto the thread, where the nuts comprise opposing flanges, such that when the nuts are screwed onto the thread on the main tube and towards each other, the flanges will be on opposing sides of the gas tight membrane such that the nuts create a gas tight connection.

The invention also provides a still further advantageous embodiment where the main tube is provided with a thread on the outside. The main tube is provided with a flange in one end, where the flange of the main tube is arranged inside the membrane, and the opposite end of the main tube is lead through an aperture in the membrane. A first nut provided with a flange, where the first nut is screwed onto the thread on the main tube, facing the flange of the first nut towards the flange of the main tube, creating a gas tight connection through the membrane. The main tube comprising the first nut is arranged inside a container, and the opposite end of the main tube is lead through an aperture in the container, where the second nut is screwed onto the main tube facing the flange of the second nut towards the container surface.

By connecting the gas tight membrane and the container with the gas indicator, the visual monitoring may be performed outside the container, directly through the window of the gas indicator. At the same time the membrane is fixed to the container through the gas indicator in one end. The membrane may also be fixed to the container by other means of fixation, preventing the membrane, thereby also the object inside the volume of the membrane, to move around inside the container, and thereby be placed in an undesirable position which may cause a safety risk.

In an advantageous embodiment the visible gas indicators fastening means to said gas tight membrane enclosing a volume containing an object, is a separate entity to the second means provided for fastening the gas indicator to a container, inside which the gas tight membrane enclosing the volume with the object is arranged, and where said fastening means is in gas communication with said second means by means of a conduit or tube.

By splitting the device in two, but retaining the gas tightness of the device, a more versatile installation/mounting is achieved. The position in the gas tight membrane may be selected completely free of which part of the enclosing container is visible. Likewise the window into the chamber may be arranged in the container in the most ideal place, in that the chamber is connected via tubes or conduits to the interface with the gas tight membrane. If a humidity sensor is provided this humidity sensor may utilize the same fastening means to said gas tight membrane enclosing a volume containing an object, by providing said fastening means with two tube/conduit connectors. The humidity connectors corresponding part—the part to be mounted in the container at the other end of the tube/conduit, may be arranged adjacent but still separate from the gas indicator.

This arrangement provides increased freedom to arrange the various parts of the device in the most opportune positions.

In a further advantageous embodiment of the invention, the inflatable life raft is of the type where a pressurized canister containing carbon dioxide is used for inflating said life raft. The life raft together with the pressurized canister is stored inside a flexible gas tight membrane, wherein a visible gas indicator is provided. The indicator comprises means for being fastened to the gas tight membrane enclosing a volume containing the life raft. The indicator comprises a chamber having a transparent window. The chamber is in gas communication with the interior of the volume, and said window is arranged outside said volume, and a substrate is arranged inside said chamber and visible from outside said volume. The substrate changes colours when exposed to a target gas.

During periodic inspections relative humidity (R.H.) and especially the carbon dioxide content of the gas inside the bag is controlled. If monitoring if the carbon dioxide cannister is leaking carbon dioxide and thereby losing the inflating capacity can be done easily, rapidly and without any tools, the inspection on site will prevent dangerous situations. The gas indicator provides an easy monitoring method by visually observing, by using amine beads, the carbon dioxide status inside the gas tight membrane which encloses a volume containing an inflatable life raft.

Amine gas treating or detecting materials refers to a group of processes that use aqueous solutions of various alkylamines, referred to as amines. The amines gas treating/acid gas removal is used in the process of removing or detecting hydrogen sulphide and/or carbon dioxide from and in gasses. Many different amines are used in gas treating, such as: Diethanolamine (DEA), Monoethanolamine (MEA), Methyldiethanolamine (MDEA), Diisopropanolamine (DIPA) and Aminoethoxyethanol (Diglycolamine) (DGA).

The amine concentration in the absorbent is an important parameter in the design and operation of an amine gas treating and detecting process. Especially in this application, the process of changing colours quickly when a target gas is detected.

The choice of amine concentration in the beads solution depends upon a number of factors and is usually made simply on the basis of experience. If the inflating gas is a mixture of gases and if, for instance, a tracer is added to the inflating gas, it is within the inventive idea that the means for measuring and/or monitoring the carbon dioxide content of the gas inside the bag as well, is capable of measuring and/or monitoring other gases or a tracer of the gas inside the bag.

Suitable beads may be obtained from for example the company Brownell.

In a still further advantageous embodiment of the invention, the life raft and pressurized canister stored inside the flexible gas tight membrane is further placed in a hard or semi-hard container where the window of the gas indicator is visible outside the container.

In order to be certain that survival devices, such as an inflatable life raft, are permanently ready for immediate use, inflatable life rafts are subject to regular periodic inspections. Inspection requires the inflatable life raft to be taken from its storage location on board a ship or vessel and to be transferred to an approved maintenance station on land. Inspection may consist, in particular, in opening the container to verify its operating state, in inflating the raft to verify that it is airtight.

DESCRIPTION OF THE DRAWING

The invention will now be described with reference to the accompanying drawings in which.

DETAILED DESCRIPTION OF THE INVENTION

The invention provides a simple and efficient solution for visual monitoring of the carbon dioxide level inside a packed inflatable life raft, by using a visible gas indicator. As already mentioned above, the invention is described with reference to an inflatable life raft, but any object sealed/packaged inside a gastight membrane, may be monitored with the present invention. An inflatable life raft is merely an example used as an example in order to describe the invention.

By using a visible gas indicator attached to the vacuum-packed inflatable life raft the monitoring is easily accessed at all times, and the periodic inspections can be prolonged, saving time and costs. Alternatively the inspections can be carried out when there is a need, i.e. when the beads change colours. Also the production process will be optimized as regards time and costs, because the visible gas indicator is easily produced and attached to the vacuum-packed inflatable life raft. Furthermore, it is possible to reuse the visible gas indicator since the carbon dioxide can easily be released from the amine in the beads, by using heat. In this way it is achieved that on the basis of the monitored environmental parameters inside the bag it is possible to evaluate the status of the life raft without unpacking and inflating the life raft.

Figure 1:
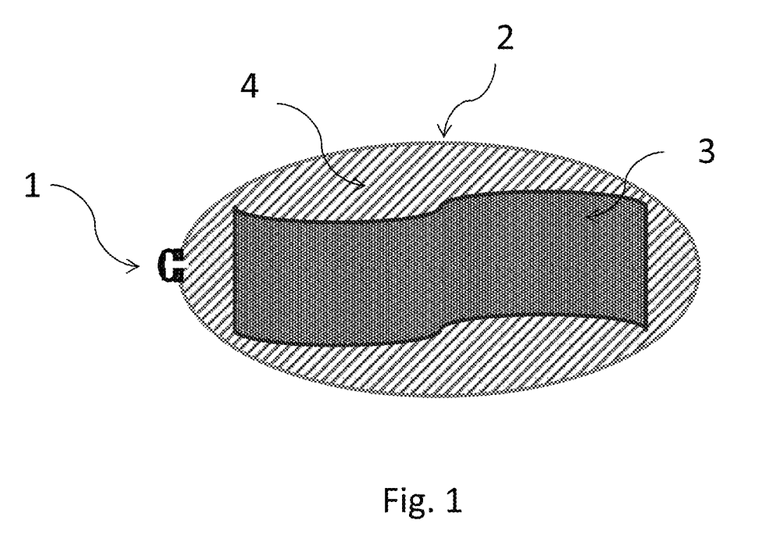
FIG. 1 shows the gas indicator fastened to a gas tight membrane enclosing a volume containing an object.

FIG. 1 shows the gas indicator 1 fastened to a vacuum-packed gas tight membrane 2 enclosing a volume 4 containing an object 3. The object inside the gas tight membrane 2 may be an inflatable life raft. The life raft is inflated by using gas, e.g. carbon dioxide. The gas is contained in a canister until the gas is released into the life raft. To prevent failure due to gas leaking during storage, a maintenance procedure is required for safety reasons. The gas indicator 1 is visible from the outside of the gas tight membrane, and in gas communication with the volume enclosed by the gas tight membrane. The gas indicator 1 is arranged in a gas tight connection to the gas tight membrane 2. If the gas is leaking from the gas canister and into the volume 4 of the gas tight membrane (2), the gas can be detected.

Figure 2:
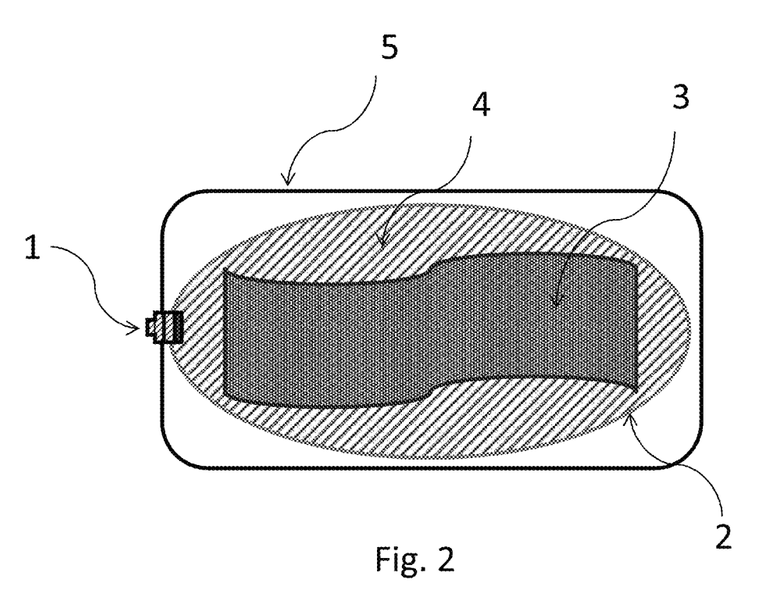
FIG. 2 shows the gas indicator fastened to a container and to a gas tight membrane enclosing a volume containing an object inside the container.

FIG. 2 shows the gas indicator 1 fastened to a container and in a gas tight connection to a gas tight membrane enclosing a volume 4 containing an object 3 inside the container 5. A life raft may be contained in a hard or semi-hard container 5, or even in a bag. The gas indicator 1 is visible from outside the container 5 and the gas indicator 1 is in gas communication with the volume 4 enclosed by the gas tight membrane 2.

The container 5 or bag may be secured on a ship or vessel, and may easily be dismounted when an accident occurs, or when the inflatable life raft 3 is to be serviced. It is also important that the gas indicator 1 is easily accessible, so a visual maintenance and monitoring of the condition can be performed quickly and smooth.

Figure 3:
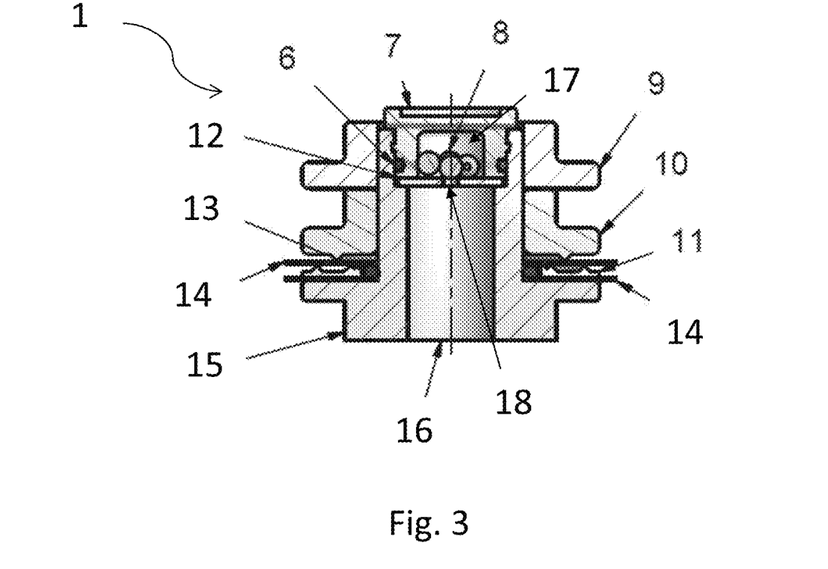
FIG. 3 illustrates a cross-section through one version of the construction of a gas indicator 1.

FIG. 3 illustrates a cross-section through one version of the construction of a gas indicator 1 according to the invention. The gas indicator 1 is provided with a main tube 15, where one end of the main tube 15 may be provided with a chamber 17 containing amine beads 8. An O-ring 6 is arranged between the chamber 8 and the main tube 15, to ensure a gas tight closure. The carbon dioxide can be detected by using amine beads 8, which change colours when the amine is in contact with a target gas, e.g. carbon dioxide. Another target gas may be detected instead of carbon dioxide, when choosing another substrate arranged inside the chamber 17. A window 7 is attached to the chamber 17 providing a visual contact to the amine beads 8 from the outside environment. The chamber 17 may also be provided with an aperture 18 in an indicator plate 12, where the indicator 12 plate is attached in the chamber 17 opposite to the window 7. The aperture 18 provides a gas communication path 16 directing the gas to the amine beads 8 in the chamber 17. The main tube 15 is provided with a thread on the outside. The main tube 15 is arranged with a flange extending radially from the opposite end to the end where the chamber 17 is attached. Optional two latex plates 14 may be arranged between the flange of the main tube 15 and the flange of the nut 10, when fastened to the membrane 2, so that one latex plate is placed on one side and the other latex plate 14 is placed on the other side of the membrane 2. An O-ring 13 is provided between the two latex plates 14, to ensure a gas tight closure. Furthermore, a sealing compound may be provided between and/or around the flange of the nut 10 and the membrane 2, and between the latex plates 14.

A first nut 9 is provided, having a flange extending radially from said nut 9. A second nut 10 is provided, having a flange extending radially from the second nut 10, where at least one side of the flange is provided with at least one bulge member 11. The second nut 10 is screwed onto the thread on the main tube 15, and turning the flange side provided with the bulge toward the flange on the main tube 15. The bulge on the flange of the second nut 10 fits into the groove on the flange of the main tube 15. When the second nut 10 is fastened to the main tube 15, the latex plate 14 and the membrane 2 is pressed together, attached between the groove and the bulge in a gas tight connection to the gas tight membrane 2. The first nut 9 may then be screwed onto the main tube 15, placed on top of the second nut 10, e.g. as a further locking procuration.

Figure 4:
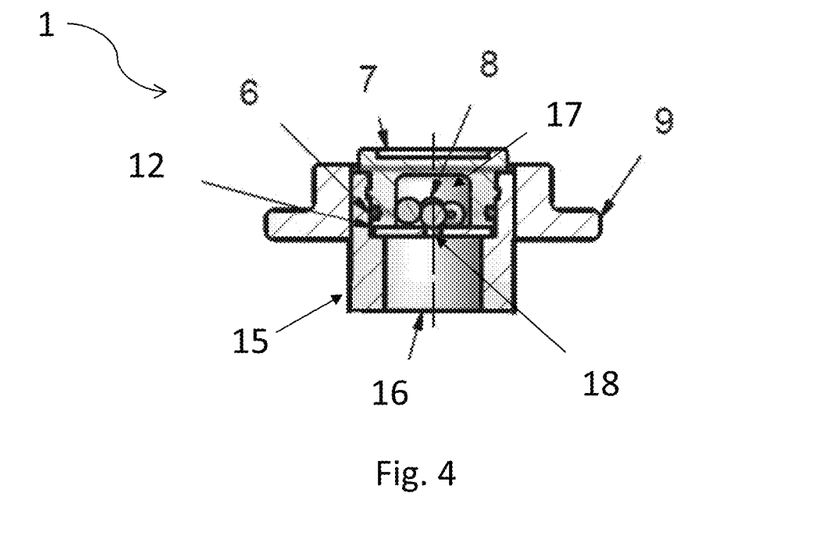
FIG. 4 shows a gas indicator containing amine beads and one nut screwed onto the thread of the main tube.

FIG. 4 shows the gas indicator 1 containing amine beads 8 and one nut 9 is screwed onto the thread of the main tube 15. Another solution may be to provide the main tube 15 with a flange extending radially similar to the nut 9. The main tube 15 is provided with a chamber 17 containing amine beads 8. A window 7 is attached to the chamber 17 providing a visual contact to the amine beads 8 from the outside environment, where the CO2 may be detected when the amine beads change colours. The chamber 17 may also be provided with an aperture 18 in an indicator plate 12, where the indicator 12 plate is attached to the chamber 17 opposite the window 7. The aperture 18 provides a gas communication path 16 directing the gas to the amine beads 8 in the chamber 17. The gas indicator 1 may be fastened to the gas tight membrane 2, using a sealing compound, ensuring a gas tight connection. The sealing may alternatively be provided by glue or by ultrasonic welding, or a similar method, also insuring a gas tight connection. The gas indicator 1 may be provided before or after the membrane e.g. encloses a volume which contains an object. Also the gas indicator 1 may be fastened by using retaining/locking ring, washer, gasket and/or O-rings, placed on both sides of the membrane 2, to ensure a firm and solid connection between the membrane 2 and the gas indicator 1.

Figure 5:
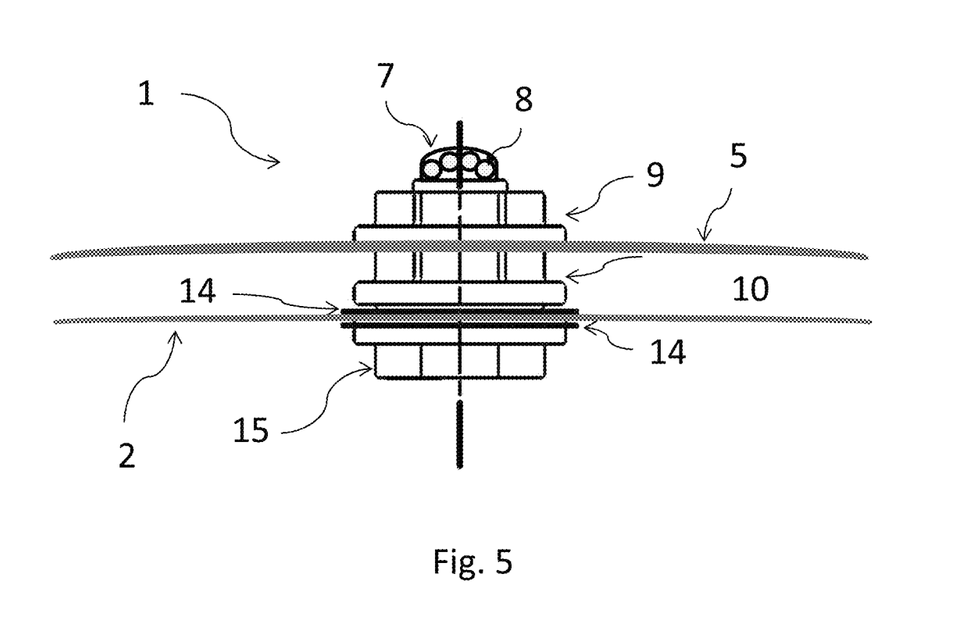
FIG. 5 shows a side view section of the gas indicator fastened to a container shell and to a gas tight membrane.

FIG. 5 shows a side view section of the gas indicator 1 fastened to a container 5 and to a gas tight membrane 2 enclosing a volume containing an object, which is located inside the container 5.

The gas indicator 1 is provided with a main tube 15, where in one end of the main tube 15 may be provided a half sphered window 7 containing amine beads 8. The amine beads 8 may be visible from a large viewing angle providing a visual contact within a long distance, which is especially important when the amine beads 8 change colours. The main tube 15 is provided with a thread on the outside. The main tube 15 is arranged with a flange extending radially from the opposite end to the end where the window 7 is attached. Optionally two latex plates 14 may be arranged so the one latex plate 14 is placed on one side of the membrane 2 and the other latex plate 14 is placed on the other side of the membrane 2. Furthermore, a sealing compound may be provided between and/or around the flange of the nut 10 and the membrane 2, and between the optional latex plates 14.

A first nut 9 is provided, having a flange extending radially from said nut 9, where the sides of the flange is substantially planed adjacent to the container 5. A second nut 10 is provided between the container 5 and the membrane 2, having a flange extending radially from the second nut 10. The second nut 10 is screwed onto the thread on the main tube 15, turning the flange toward the flange on the main tube 15. When the second nut 10 is fastened to the main tube 15, the optional latex plate 14 and the membrane 2 is pressed together, in a gas tight connection to the gas tight membrane 2. Now a gas communication is provided, from the volume containing an inflatable life-raft inside a gas tight membrane 2, through the container 5 wall, so the gas status may be monitored visually from the outside of the container 5.

In principle, the amine beads 8 may be placed directly inside the gas tight membrane 2. To ensure a clear and visual contact from the outside, the amine beads 8 are arranged outside the gas tight membrane 2 in a gas indicator 1, where the amine beads 8 may easily be monitored at all time.

In marine applications, corrosion resistance in contact with sea water must be high, otherwise the product, e.g. the gas indicator 1, cannot be considered corrosion proof in all situations. They are susceptible to localized attack mechanisms, principally cracking and pitting corrosion. When producing the gas indicator 1, the range of material is restricted, when the gas indicator 1 is used in applications where the gas indicator 1 may be in direct or indirect contact with a harsh environment, such as sea water.

Figure 6:
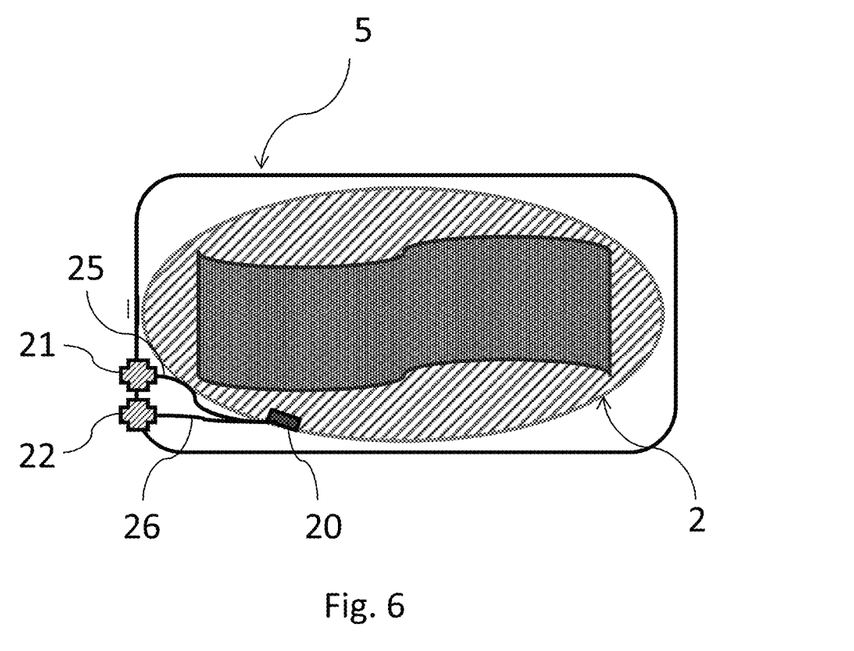
FIG. 6 shows a further embodiment of the invention.

In FIG. 6 is illustrated a further embodiment of the invention. In addition to measuring/detecting a target gas it is also often desirable to detect moisture inside a container. The presence of moisture is often detrimental to the contents. For example in a life raft moisture may damage emergency flares, food supply and other vital contents. For these purposes humidity indicators may also be provided in the gas tight membrane. These humidity indicators are designed to also change color at a certain predetermined humidity. The problem with humidity is that the humidity also depends on the temperature, and therefore the humidity sensor must be adapted to a given temperature interval. However, one type of existing humidity sensors/indicators, available from Thanner A/S, changes color when exposed to humidity. These indicators are available for indication of various moisture levels for example 40% and 60% relative humidity. In the indicators are provided a base material (paper) impregnated with a compound, which changes color when moisture is present. Consequently such an indicator will also be suitable for mounting in the gas tight membrane, being visible from the outside.

Figure 7:
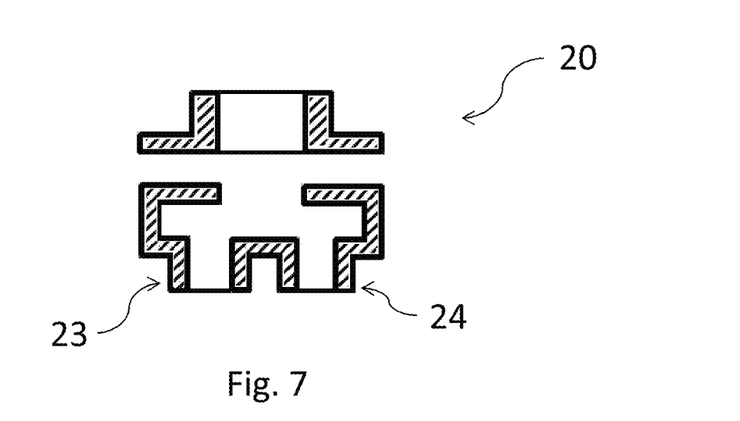
FIG. 7 shows connection part.

In FIG. 6, the gas indicator comprises two parts, a first connection part 20 providing a connection to the inner of the gas tight membrane 2, and a second part 21, 22 suitable to be fastened to an outer container 5 or membrane. The first connection part 20 may be constructed and fastened to the gas tight membrane as described above with reference to FIG. 3 or 5. The first connection part 20, see FIG. 7 may be provided with nut and flanges as discussed above with respect to FIGS. 3 and 5 in order to establish a gas tight connection through the membrane 2 (not illustrated). The first connection part 20 is furthermore provided in this example with two tube connections 23, 24. Any number may be provided but typically it is only desirable to have one or two tube connections: one for the gas indicator and one for the humidity indicator. Obviously if one or more tube connectors are not used they shall be sealed in a gas tight manner as not to provide an open aperture to the inside of the gas tight membrane.

The second connection part 21, 22 will contain the gas indicator chamber 17, as explained with reference to FIGS. 3, 4 and/or 5. In order to be able to connect the first and second connection parts 20, 21, 22 a number of conduits/tubes 25, 26 (see FIG. 6) are provided. The conduits/tubes must be gas proof. In this manner a very versatile construction is provided.

The invention claimed is:

1. Visible gas indicator, where said indicator comprises fastening means for a gas tight membrane enclosing a gas evacuated volume containing an object, where said gas indicator comprises a chamber having a transparent window, wherein the gas indicator has a main tube provided with a thread and at least one nut, where the window is arranged in a first end of the main tube, where said chamber is in gas communication through said main tube with the interior of the volume, and said window is arranged outside said volume, and where a substrate is arranged inside said chamber so that the substrate in said chamber is visible through the window, where the substrate contains amines, where said substrate changes colours when exposed to a target gas.

2. Visible gas indicator according to claim 1, wherein said main tube is provided with a thread on the outside, and where two nuts can be screwed onto the thread, where the nuts comprise opposing flanges, such that when the nuts are screwed onto the thread on the main tube and towards each other, the flanges will be on opposing sides of the gas tight membrane such that the nuts create a gas tight connection.

3. Visible gas indicator according to claim 1, wherein where a second end opposite said first end a flange is arranged extending radially away from said main tube.

4. Visible gas indicator according to claim 3, wherein the main tube between the flange and a distance towards the window is provided with a thread, and a nut having a flange extending radially from said nut is screwed onto the thread on the main tube, such that the gas tight membrane material may be arranged between the flange on the main tube and the flange on the nut.

5. Visible gas indicator according to claim 1, wherein in addition to the fastening means to a gas tight membrane enclosing a volume containing an object, a further second means are provided for fastening the gas indicator to a container inside which the gas tight membrane enclosing the volume with the object is arranged, said window being visible on the outside of the container.

6. Visible gas indicator according to claim 5, wherein the second means comprises one or more second set of nuts which may be screwed onto the thread on the main tube.

7. Visible gas indicator according to claim 1, wherein the material of the gas indicator is produced from at least one material selected from the group of stainless steel, aluminum, plastic, polymers.

8. Method of providing a visible gas indicator according to claim 1, wherein the gas indicator is visible from the outside of a gas tight membrane comprising an enclosed gas evacuated volume, wherein a target gas is carbon dioxide and a substrate contains amines and where said visible gas indicator comprises a chamber having a transparent window, where said chamber is in gas communication with the interior of the volume, and said window is arranged outside said volume, and where the substrate is arranged inside said chamber and the substrate is visible through the transparent window from outside said volume, where said substrate changes colours when exposed to carbon dioxide, where said gas indicator has a main tube, where the window is arranged in a first end of the main tube, and where a flange is provided extending radially from the main tube such that a gas tight connection is established between the flange and a membrane.

9. Method of providing a visible gas indicator according to claim 8, wherein the main tube is provided with a thread on the outside, and where two nuts can be screwed onto the thread, where the nuts comprise opposing flanges, such that when the nuts are screwed onto the thread on the main tube and towards each other, the flanges will be on opposing sides of the gas tight membrane such that the nuts create a gas tight connection.

10. Method of providing a visible gas indicator according to claim 8, wherein the main tube is provided with a thread on the outside, where said main tube is provided with a flange in one end, where the flange of the main tube is arranged inside the membrane and the opposite end of the main tube is lead through an aperture in the membrane, and a first nut provided with a flange, where the first nut is screwed onto the thread on the main tube, facing the flange of the first nut towards the flange of the main tube, creating a gas tight connection through the membrane, where the main tube comprising the first nut is arranged inside a container, and the opposite end of the main tube is lead through an aperture in the container, where the second nut is screwed onto the main tube facing the flange of the second nut towards the container surface.

11. Inflatable life raft of the type where a pressurized canister containing carbon dioxide is used for inflating said life raft, where the life raft together with the pressurized canister is stored inside a flexible gas tight membrane, wherein a visible gas indicator according to claim 1 is provided, where said indicator comprises means for being fastened to the gas tight membrane enclosing a volume containing the life raft, where said indicator comprises a chamber having a transparent window, where said chamber is in gas communication with the interior of the volume, and said window is arranged outside said volume, and a substrate is arranged inside said chamber and visible from outside said volume, where said substrate changes colours when exposed to a target gas.

12. Inflatable life raft according to claim 11, wherein the life raft and pressurized canister stored inside the flexible gas tight membrane are further placed in a hard or semi-hard container, and where the window is visible outside the container.

* * * * *